United States Patent [19]

Van Iderstine

[11] Patent Number: 4,504,129
[45] Date of Patent: Mar. 12, 1985

[54] PHOTOGRAPHY ADAPTOR ASSEMBLY FOR A SLIT LAMP EXAMINATION UNIT

[76] Inventor: Richard Van Iderstine, 10806 Stone Canyon Rd., #2118, Dallas, Tex. 75230

[21] Appl. No.: 351,672
[22] PCT Filed: May 26, 1981
[86] PCT No.: PCT/US81/00694
  § 371 Date: Jan. 8, 1982
  § 102(e) Date: Jan. 8, 1982
[87] PCT Pub. No.: WO81/03417
  PCT Pub. Date: Dec. 10, 1981

Related U.S. Application Data

[63] Continuation-in-part of Ser. No. 153,209, May 27, 1980, abandoned.

[51] Int. Cl.³ .................................................. A61B 3/14
[52] U.S. Cl. .................................. 351/206; 351/214; 351/221
[58] Field of Search ........................ 351/214, 206, 221

[56] References Cited

U.S. PATENT DOCUMENTS 3,944,342  3/1976  Martinez ............................. 351/214

OTHER PUBLICATIONS

Topcon, Tokyo Optical, Tokyo, Japan.

Primary Examiner—Rodney B. Bovernick
Assistant Examiner—P. M. Dzierzynski
Attorney, Agent, or Firm—Drude Faulconer

[57] ABSTRACT

An assembly for adapting any of several different models of commercially-available slit lamps (10) into an optic examination unit capable of being used for routine eye examinations and also capable of taking high quality photographs of what is being viewed through an ocular of the slit lamp. The assembly is comprised of an illumination means (30a, 30b, 30c) having both a steady light source (69) and a strobe source (80), a camera support arm (55) for supporting a camera (57) in proper position for taking photographs through an ocular (26a) of the slit lamp, an eyepiece adaptor housing (59) and a camera sleeve (56) adapted to be connected into the lens receiving opening of the camera.

To assemble the present invention into a slit lamp, the original light source of the slit lamp is removed and is replaced with the present illumination source. The original eyepiece housing is removed and is replaced with the present eyepiece adaptor housing. The camera support arm is mounted on the microscope support of the slit lamp and the camera sleeve which is positioned into a ring clamp carried by the camera support arm is attached to the lens receiving opening of a camera back. The camera support arm is manipulated to cause the camera sleeve to move over the eyepiece adaptor housing so that the camera is now in position to photograph through the ocular of the slit lamp.

23 Claims, 15 Drawing Figures

PHOTOGRAPHY ADAPTOR ASSEMBLY FOR A SLIT LAMP EXAMINATION UNIT

This is a continuation-in-part of application Ser. No. 153,209 filed May 27, 1980 and now abandoned.

DESCRIPTION

1. Technical Field

This invention relates to optical apparatus used for examination of the human eye, commonly known as a "slit lamp", and more particularly relates to apparatus for adapting commercially-available slit lamps into a unit which is capable of photographing the eye during an examination while completely maintaining the original utility of the slit lamp.

2. Background of Invention

An optical apparatus, commonly known in the art as a slit lamp, is routinely used by ophthalmologists and/or optometrists to examine the human eye. A slit lamp provides an illumination beam having a slit image of varying widths and includes a microscope for examining the area of the eye illuminated by the beam. The illumination beam is normally directed toward the eye along a horizontal optical axis by reflecting a vertical illumination beam with a 45° reflecting mirror.

In recent years, a desire, if not a need, has arisen to record on film certain aspects of a slit lamp eye examination to aid the examiner in later treatment of the eye and/or to provide him with a permanent visual history of a patient's eye condition. To provide the high quality photographs desired for these purposes, special slit lamps having built-in photographic capabilities have been developed and are now commercially available. However, these "photo slit lamps" are especially designed and must be purchased as a complete new unit. Since most presently practicing ophthalmologists and optometrists already own one or more standard slit lamps, it can be seen that considerable expense would be involved in converting over to these special photography slit lamps. Further, since the examiner is familiar with dioptric settings, etc., of his own slit lamp and is comfortable with its use, the purchase of a new photography slit lamp requires him to start over in establishing his examination procedures and in gaining confidence therein.

Other devices have been proposed for adapting existing, standard slit lamps so that they may also be used to take photographs of the eye. One such device comprises a sleeve which merely attached a camera to the ocular of the slit lamp. Unfortunately, however, the illumination of the standard slit lamp is not sufficient under normal conditions to permit the taking of high-quality photographs. Further, the sleeve is relatively difficult to attach to and detach from the slit lamp which may cause delays in a routine examination. Still further, proper focusing of the camera once it is in position involves a relatively complicated procedure requiring considerable time and effort on the part of the examiner. Still further, the ocular, itself, must support the entire weight of the camera.

Another known adaptor device merely involves mounting an arm on the slit lamp which carries a camera with a flash attachment thereon for photographing the anterior portions of the eye. In addition to requiring the normally present tonometer to be removed from the slit lamp each time a picture is to be taken, the picture itself is not taken through the ocular of the lamp and accordingly does not record what is being seen by the examiner.

Therefore, it should be recognized that a need exists for a means by which an existing slit lamp can be adapted into a unit capable of taking high quality photographs through the ocular of the slit lamp while, at the same time, allowing the slit lamp to maintain all of its original features necessary for performing a routine eye examination without requiring the constant assembling and disassembling of parts during an examination.

DISCLOSURE OF THE INVENTION

The present invention provides a means for adapting a commercially-available slit lamp into a unit capable of being used for routine eye examinations and also capable of taking high quality photographs of what is being viewed through an ocular of the slit lamp. The present invention comprises an assembly of several components which can be quickly and easily installed onto a commercial slit lamp and indefinitely left in place on the slit lamp even when the slit lamp is used for routine examinations.

More specifically, the present invention comprises a new and improved illumination source, a camera support arm, a camera sleeve, and an eyepiece adaptor housing, all of which are adapted to be assembled onto a commercial slit lamp. The illumination source which easily fits onto the illumination column of a slit lamp is adapted to replace the original constant light source of the slit lamp after the original light source and condenser lens are removed from the column. The illumination source contains both a constant light source, e.g. halogen bulb, for routine examination and a flash light source, e.g. xenon strobe, for use in photographing the eye.

The camera support arm has a clamp which is adapted to be connected to the support on the slit lamp which supports the microscope. A pivot pin on an articulated frame of the camera support arm is rotatably mounted in the clamp so that the frame can freely rotate with respect to the clamp. A ring clamp is carried by a vertical adjustment means mounted on the outer end of the articulated frame. The camera sleeve which is adapted to be connected into the lens receiving opening of a commercially-available camera is adapted to be received into the ring clamp and is thereby supported on camera support arm.

The eyepiece adaptor housing is adapted to replace the original eyepiece housing of one of the oculars of the microscope to thereby provide a flush surface around the eyepiece onto which the camera sleeve is positioned when the camera is moved into an operable position. Camera sleeve is tightened onto adaptor housing to thereby exclude external light from the camera. When the camera is in position, the ocular through which a photograph is to be taken can still be focused in the same manner as it could be originally. By taking the photograph through the ocular, the original full range of magnification is available for photographing the eye.

The components may be assembled into a slit lamp before the slit lamp is sold or preferably the components are assembled into a kit and sold to practitioner who can easily assemble the components into his own slit lamp. In addition to the savings involved, the practitioner can continue to use his own slit lamp with which he is familiar. The individual components are designed so most of the components will fit without modification into several different standard commercial slit lamps. Where a modification is required due to a slightly different configuration of a particular commercial slit lamp, the modification involves only a slight change in the dimensions or configuration of that component so that it fits that particular slit lamp.

Further, the components are designed so that once assembled, they may remain in place on the slit lamp indefinitely and do not interfere with the use of the slit lamp in performing a routine examination. However, if desired, the camera can easily be removed for other use or the camera and camera support arm can easily be removed when not in use.

BRIEF DESCRIPTION OF THE DRAWINGS

The actual construction, operation, and the apparent advantages of the present invention will be better understood by referring to the drawings in which like numerals identify like parts in the different figures and in which.

BEST MODES FOR CARRYING OUT THE INVENTION

Figures 1, 2:
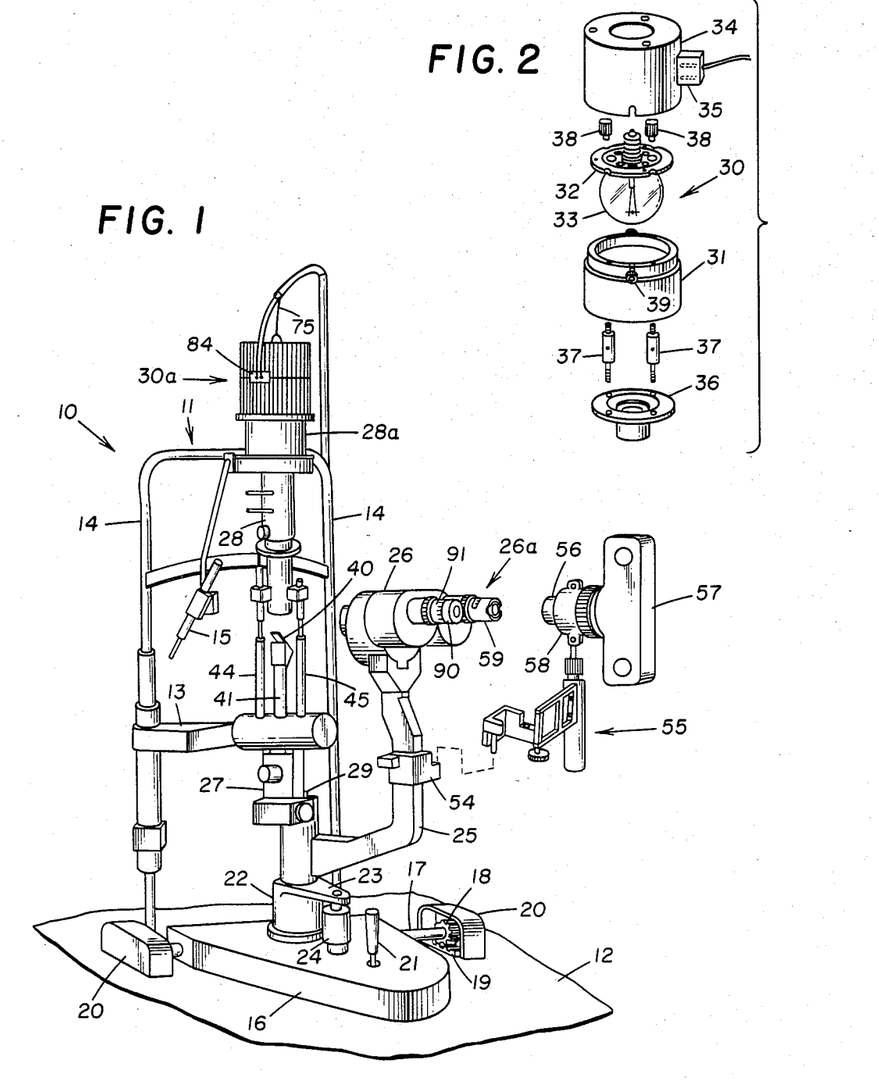
FIG. 1 is a perspective view of a commercially-available slit lamp onto the present invention has been incorporated.
FIG. 2 is an exploded, perspective view of the components of the origianl light source of the slit lamp of FIG. 1.

Referring more particularly to the drawings, FIG. 1 discloses slit lamp 10 which is illustrative of several commercially-available slit lamps into which the present invention can be incorporated. Typical examples of such slit lamps are (1) Topcon Slit Lamp, Model SL-3D, Topcon Instrument Corp. of America, Paramus, N.J.; (2) Mentor Slit Lamp, Mentor Division of Codman and Shurtleff, Inc., Randolf, Mass.; (3) Marco V Slit Lamp, MARCO, Jacksonville, Fla.; (4) Model 900, Haag-Streit, Bern, Switzerland. Representative slit lamp 10 is comprised of a head rest frame 11 mounted on table 12. Chin support 13 extends between parallel uprights 14 of frame 11 and is vertically adjustable to permit proper alignment of a patient's eye. Fixation light 15 depends from head rest frame 11 and, as is well known, is adapted to be positioned for maximum benefit during an examination.

Carriage 16 is mounted on table 12 for relative movement in relation to frame 11 by means of an element (not shown) which is mounted in carriage 16 and which rides on the surface of table 12. Carriage 16 moves laterally along rod 17 which in turn have pinions 18 (only one shown) on the ends thereof. Pinions 18 mate with racks 19 (only one shown) formed within housings 20 which are mounted on table 12. A control lever or "joy stick" 21 extends from carriage 16 and is used to provide horizontal movement and fine focus of slit lamp 10.

Mounted on carriage 16 is a pivot assembly 21 which includes hub 22 having arm 23 extending therefrom and cooperating with vertical adjustment knob 24 for raising and lowering the pivot assembly 21. Pivot assembly 21 includes microscope support arm 25 which carries a binocular microscope body 26 and an illumination arm 27 which carries an illumination column 28, arms 25 and 27 both being pivotably mounted on a vertical pivot pin 29 which is supported by hub 22 so that microscope body 26 and illumination column 28 are both pivotable about the same axis.

In a typical, standard slit lamp, of the type being described, original lamp unit 30 (see FIG. 2) is mounted atop illumination column 28. Lamp unit 30 is comprised of a lower housing 31, a perforated centering plate 32 which carries an incandescent bulb 33, and a contact cap 34 having an electrical power connection 35 thereon. As will be understood by those skilled in this art, condensing lens 36 (FIG. 2) normally sets within column 28 at its upper end 28a (FIG. 1) and is held in position by four equally spaced studs 37 (only two shown in FIG. 2) which are threaded into upper column end 28a and extend upward therefrom. Housing 31 is positioned over studs 37 and plate 32 with bulb 33 is positioned onto the top of housing 31 and over studs 37. Nuts 38 are then threaded onto the top of studs 37 to secure the components in a fixed relationship on column 28. Cap 34 is positioned onto housing 31 and is held in place by set screw 39. A contact (not shown) in cap 31 contacts the top of bulb 33 to supply power therethrough through connector 35.

Bulb 33 directs a vertical beam of light through condenser lens 36 toward mirror 40 which is disposed at the bottom of the illumination column 28 on a post 41 in substantially horizontal, axial alignment with microscope 26 and oriented at substantially 45° to direct the light beam toward the eye of a patient.

Illumination column 28 is supported on the illumination arm 27 by a pair of spaced columns 44 and 45. As understood in the art, upper column end 28a has a pair of cooperating members below bulb 33 and condensing lens 36 which are controlled by a cam and control rod (not shown) to form a slit diaphragm for adjusting the width of the slit of light used during an examination. The actual adjusting of the slit is accomplished by turning knob 46 which is located on illumnating arm 27. As explained above and as will be recognized by those skilled in the art, the details of slit lamp 10 as described up to this point are all well known in the art.

Figure 3:
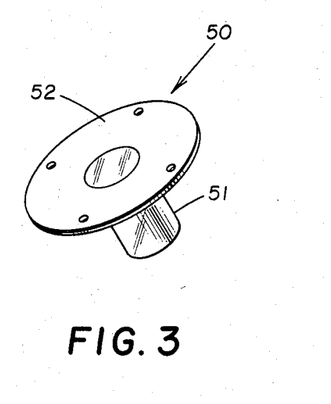
FIG. 3 is a perspective view of a light pipe for use in present invention.

Commercially-available slit lamp 10 as shown in FIG. 1 has been adapted in accordance with the present invention to include the capability of photographing the anterior segment and/or the interior segment of a patient's eye during an examination. The original light source 30 has been removed and replaced with a first embodiment 30a of the illumination means of the present invention. To do this, original cap 34, plate 32 and bulb 33, housing 31, condensing lens 36, studs 37, and nuts 38 (FIG. 2) are all removed from lamp 10. A light distributing means, e.g. light pipe 50 (FIG. 3) comprising a solid glass rod 51 centrally mounted in plate 52 may be placed onto upper end 28a of illuminating column 28 in the same position formally occupied by condensing lens 36. It should be understood that other known light distributing means, e.g. a flat sheet of clear or frosted glass (not shown), may also be used to replace condensing lens 36 or condensing lens may be dispensed with altogether without departing from the present invention.

Illumination means 30a, the details of which will be discussed below, is then mounted onto the upper end 28a of column 28. Two other embodiments 30b, 30c of the illumination means of the present invention will also be described in more detail below. Each of the embodiments 30a, 30b, 30c of illumination means contains a constant light source for routine examinations and a flash strobe light for photographing the eye of a patient.

Figure 4:
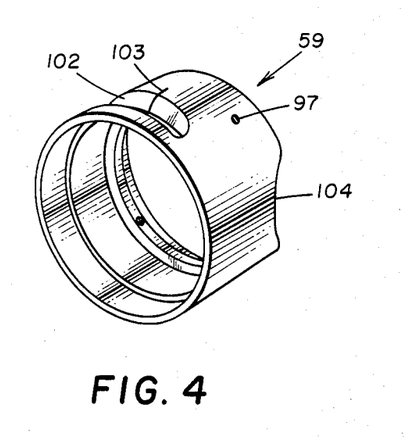
FIG. 4 is a perspective view of the eyepiece adaptor housing which forms a part of the present invention.
Figure 5:
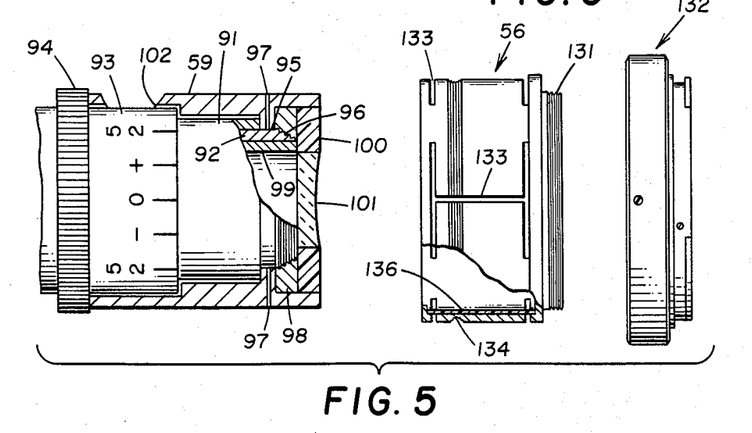
FIG. 5 is an exploded view, partly in section, of the ocular of the slit lamp of FIG. 1 with eyepiece adaptor housing in place, the camera sleeve of the present invention, and a commercially available T-adaptor for a camera.

Clamp 54 (FIG. 1) is affixed to microscope support arm 25 and camera support arm 55 is pivotably mounted thereto. Camera sleeve 56 is attached to the lens receiving opening in commercially-available camera back 57 and is mounted into ring clamp 58 of camera support arm 55. Sleeve 53 is adapted to receive ocular 26a of microscope 26 when camera support arm 55 is amnipulated into an operable position. In accordance with the present invention, ocular 26a has been modified by removing the original ocular housing 90 and replacing it with an ocular adaptor housing 59 (FIG. S1, 4 and 5). Adaptor housing 59 is adapted to smoothly and snuggly fit within sleeve 53 when the camera is moved into an operable position. Now that the whole of the present invention has been disclosed, each of the individual components thereof will now be described in detail under its appropriate heading.

Illumination means 30a, 30b, 30c

Referring now to FIGS. 6–9, a first embodiment 30a of illumination means is comprised of a housing which, in turn, comprises a lower strobe section 60 and an upper lamp section 61. Both sections 60, 61 are constructed from a heat resistive and insulative material, e.g. phenolic resin, and are formed with heat dissipating fins 62 along the outer surface thereof and with heat riser passages 63 along the inner surfaces thereof, said fins 62 and passages 63 on section 60 aligning with said fins 62 and passages 63, respectively, on section 61 when sections 60 and 61 are mated in an operable position.

Figure 6:
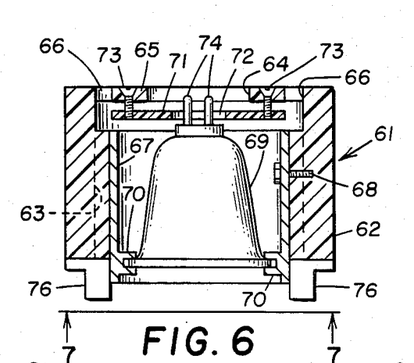
FIG. 6 is a sectional, elevational view of the upper section of one embodiment of the illumination source of the present invention.
Figure 7:
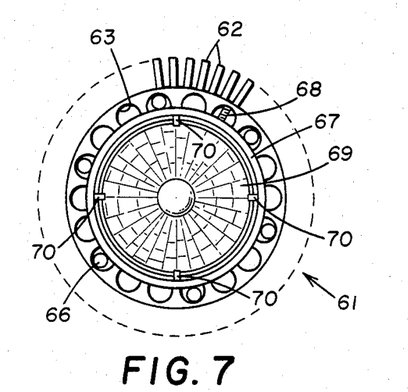
FIG. 7 is a plan view taken along line 7—7 of FIG. 6.

Upper lamp section 61, as illustrated, has a central opening 64 in top 65 thereon which is surrounded by plurality radially-spaced heat outlets 66. Positioned along the inner surface of section 61 is reflector sleeve 67 which is held in place by screws 68 or the like. Lamp 69, e.g. 10.8 volt, 42 watt, halogen-cycle, multi-mirror reflector projector lamp, Model EPT, General Electric Co., is positioned within reflector sleeve 67 and is held in place by means of four equally spaced ears 70 which are punched out of sleeve 67 or otherwise secured thereto. Light shield 71 having an opening 72 therethrough is suspended by screws 73 or the like below central opening 64 to block passage of light but allow heat to escape therethrough. Contacts 74 on lamp 69 extend through opening 72 and are adapted to be connected to power source through leads 75 (FIG. 1). The lower end of upper lamp section 61 is recessed at 76 which is adapted to frictionally fit into internal groove 77 on the top of lower strobe section 60 to secure the two sections together.

Figure 8:
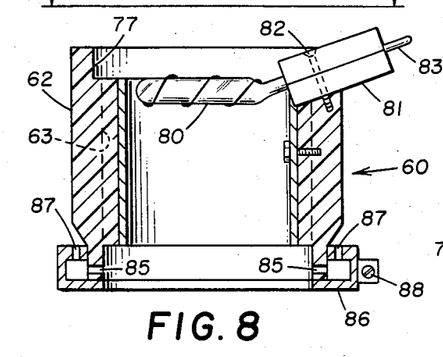
FIG. 8 is a sectional elevational view of lower section of one embodiment of the illumination source of the present invention.
Figure 9:
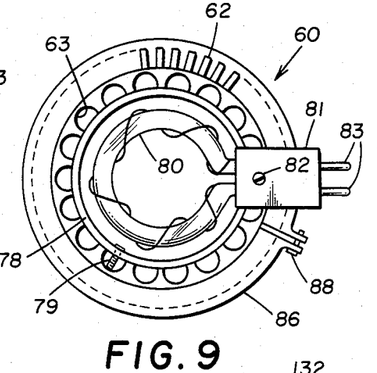
FIG. 9 is a plan view taken along line 9—9 of FIG. 8.

Lower strobe section 62 has reflector sleeve 78 secured inside thereof by means of screws 79 or the like. Ring strobe 80, e.g. xenon ring-type strobe flash capable of developing up to at least 200 watt-seconds or greater, is effectively centered in lower section 60 and is secured therein by means of insulator 81 and screw 82 threrethrough. Contacts 83 on strobe 80 extend through insulator 81 and are adapted to be connected to a power source 84 (FIG. 1). The lower end of lower strobe section 60 is beveled and has a plurality of spaced passages 85 therethrough. Split intake manifold ring 86 having a plurality of spaced inlets 87 through its upper surface is positioned on the lower beveled end of lower section 62 and is held in position by screw 88.

To assemble illumination means 30a, recess 76 on upper section 61 is frictionally fitted into recess 77 on lower section 60. When illumination means 30a is in an operating position on column 28 of slit lamp 10 and lamp 69 is activated, air within illumination means 30a will become heated and will rise within heat riser passages 63 thereby carrying heat with the air out of the interior of illumination means 30a through openings 66 in the top thereof. As the air within illumination means 30a rises, additional air is drawn into means 30 through intake manifold ring 86 via openings 87 in ring 86 and passages 85 in beveled end of lower strobe section 60. This flow of air dissipates a substantial amount of the heat generated by lamp 69 and strobe 80 and thereby maintains the heat within means 30a at safe, operational level.

Figure 11:
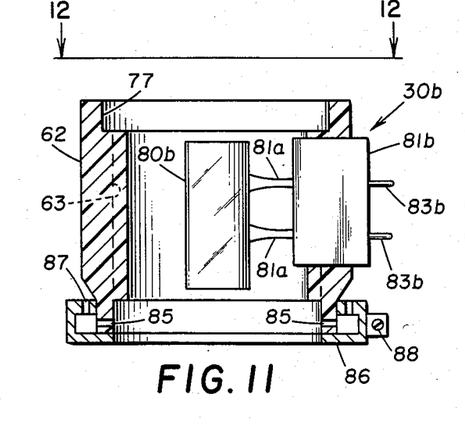
FIG. 11 is a sectional elevational view of another embodiment of the lower section of the illumination source of the present invention.
Figure 12:
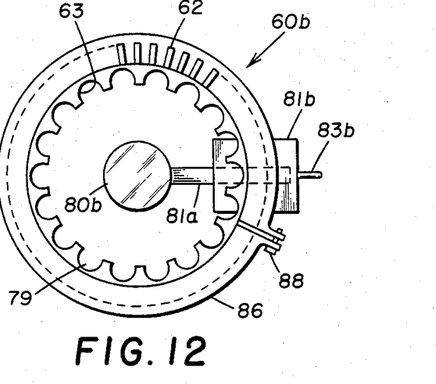
FIG. 12 is a plan view taken along line 12—12 of FIG. 11.

Another embodiment 30b of the illumination means is disclosed in FIGS. 11 and 12, wherein means 30b is comprised of a housing which, in turn, comprises a lower strobe section 60b and the same upper lamp section 61 as shown in FIGS. 6 and 7 and fully described above. The primary support structure of lower strobe section 60b is constructed similarly as is section 60 described above in that it has heat dissipating fins 62 along the outer surface thereof, heat riser passages 62 along the inner surfaces thereof, and manifold ring 86 and associated passages 85, 87 thereon.

Barrel strobe 80b (e.g. a ¾ inch diameter glass cylinder, approximately 2 inches long, filled with xenon gas and capable of developing up to at least 200 watt-seconds or greater) is supported within lower section 60b by tubular supports 81a and secured therein by means of insulator 81b. Contacts 83b for strobe 80b extend insulator 81b and are adapted to be connected to a power source (not shown). Barrel strobe 80b is constructed so that its upper and lower surfaces are flat and as optically pure as possible so that when section 60, 61 are assembled, the light from lamp 69 can pass undistorted downward through strobe 80b. Further, a sleeve of reflective material (not shown) may be positioned around strobe 80b to increase the usable light from the strobe.

Still another embodiment 30c of the illumination means 30c is comprised of a housing which, in turn, is comprised of a main support 90 having a plurality of holes 91 therein aligned in the same pattern as the original studs 37 (FIG. 1) of slit lamp 10. Ring-like strobe 80c is suspended from main support 90 by means of strobe support 92. As illustrated, strobe 80c is comprised of glass tubing (e.g. 4 millimeters in diameter) formed in a ring having an internal diameter of approximately 12 millimeters. The ends of the ring terminate in larger diameter tubing sections 93 (e.g. 6 millimeter) which have electrodes 94 therein. Sections 93 are mounted in insulator 81c which in turn is attached to strobe support 92. Strobe 80c is filled with xenon gas and is capable of developing up to at least 200 watt-seconds or greater. Contacts 83c for strobe 83b extend through insulator 81c and are adapted to be connected to a power source (not shown).

Figures 13, 14, 15:
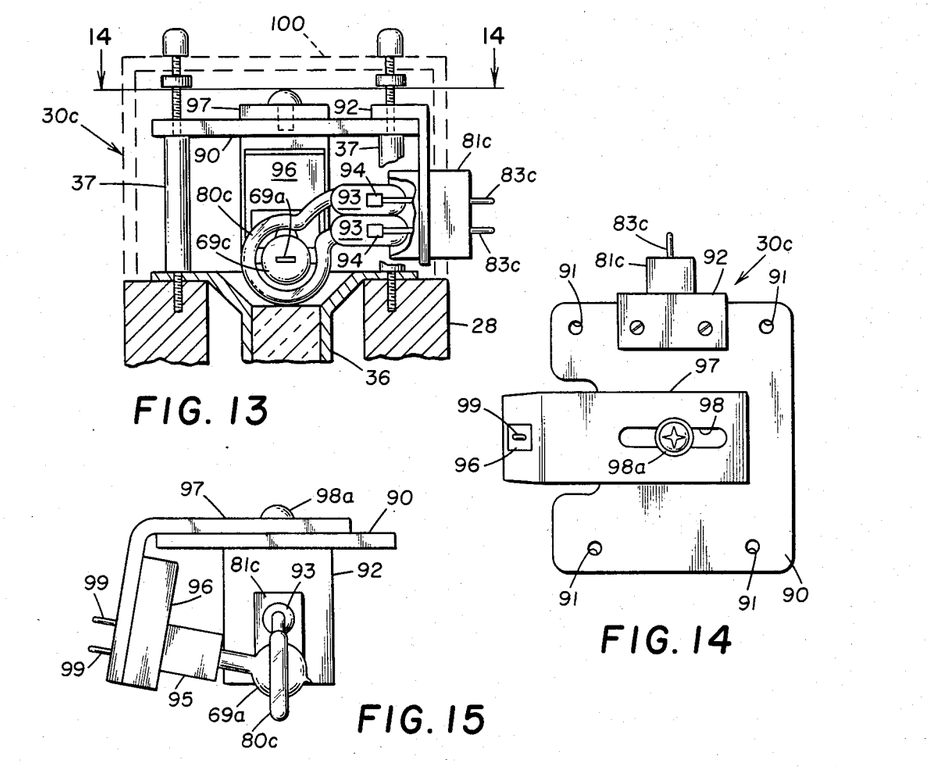
FIG. 13 is an elevational view, partly in section, of still another embodiment of the illumination source of the present invention.
FIG. 14 is a plan view taken along line 14—14 of FIG. 13.
FIG. 15 is a side view of the illumination source of FIGS. 13 and 14.

Also, suspended from main support 90 is lamp 69c, e.g. 10.8 volt, 42 watt, halogen-cycle bulb such as a General Electric Co. Model EPT lamp with the reflector removed. Lamp 69c is mounted in socket 95 or the like which, in turn, is secured to insulator 96. Insulator 96 is mounted on lamp support 97 which is mounted for slidable adjustment on main support 90 by means of slot 98 and screw 98a. Contacts 99 from lamp 69c extend through insulator 96 and are adapted to be connected to a power source. Lamp 69c extends through the center of strobe 80c when in position.

To assemble illumination means 30c on slit lamp 10 condensing lens, e.g. original condensing lens 36 (FIG. 1) is positioned on illumination column 28 and studs 37 are screwed therethrough. Holes 91 in main support 90 are positioned onto the upper ends of studs 37. Lamp support 97 is constructed so that when main support 90 is in place on studs 37, the filament 69d (FIG. 13) of lamp 67c is positioned at its appropriate focal length from lens 36. Screw 98a can be loosened and lamp support 92 is moved to center filament 69d of lamp 69c with relation to lens 36 to achieve maximum usable light for slit lamp 10. Screw 98a is then tightened to lock lamp 67c in place and a protective cap 100 (shown in dotted lines in FIG. 13) is placed over means 30c.

Ocular Adaptor Housing 59

In a commercially available slit lamp of the type described above, each of the oculars of the microscope 26 has an ocular housing 90 (FIG. 1) which forms a part of the ocular. In accordance with the present invention, ocular housing 90 from one of the oculars (shown as right ocular 26a in FIG. 1) is replaced with ocular adaptor housing 59 (FIGS. 1, 4 and 5). Referring now to FIG. 5, the terminal end of ocular 26a with adaptor housing 59 in place is described.

Eyepiece adjustment ring 91 which is used for focusing ocular 26a is rotatably mounted on cylindrical support 92 and, as illustrated, is comprised of stepped portion 93 having dioptric indicia thereon and an integral knurled ring 94. Support 92 which extends beyond eyepiece adjustment 91 has a short flat portion 95 and a threaded outer end 96. Adaptor housing 59 has a contoured interior to conform with eyepiece adjustment ring 91 so that ring 91 will rotate freely within housing 59 when said housing is in place. Adaptor housing 59 has two diametrically opposed set screw 97 which engage flat portion 95 of support 92 to prevent rotation of housing 59.

Retainer ring 98 which originally held ocular housing 90 in place on support 92 is again threaded onto threaded end 96 to thereby secure adaptor housing 59 in position. Tube 99 of original eyepiece 100 is slidably positioned within support 92 and ocular 26a is now assembled for use. Eyepiece 99 has lens 101 centered therein as well understood in the art.

Adaptor housing 59 (FIG. 4) has a slot 102 through its upper surface to expose the dioptric indicia on eyepiece adjustment ring 91 when housing 59 is in place. Base mark 103 is provided at the back of slot 101 for referencing the dioptic indicia and is in the same position as was the base mark (not shown) on original ocular housing 90. A groove (not shown) is provded internally in adaptor housing 59 which cooperates with an index pin (not shown) on support 92 to insure accurate alignment of base mark 102 when ocular 26a is assembled. Adaptor housing 59 is also recessed on its sides to aid in positioning and removing eyepiece 99 therein.

Clamp 54, Camera Support Arm 55, and Camera Sleeve 56

Clamp 54 (FIGS. 1 and 10) is illustrated as a C-shaped housing 110 which is adapted to fit onto microscope support arm 25 and is held in a fixed position thereon by means of screws 111 of the like. Since the dimensions of microscope support arm 25 may vary between various commercial models of slit lamp 10, clamp 54 may also be constructed in two parts (not shown) and assembled by means of bolts or the like so that one clamp will fit several models. Housing 110 has a projecting portion 112 extending from the side thereof which in turn has a vertical passage 113 therein adapted to rotatably receive pivot pin 114 on camera support arm 55.

Figure 10:
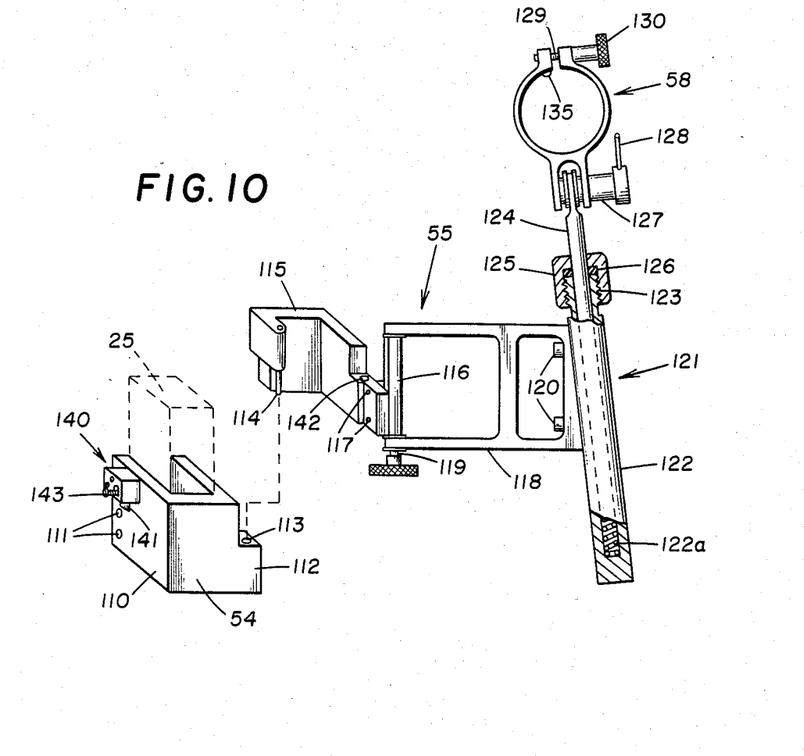
FIG. 10 is an exploded, perspective view of the camera support arm of the present invention.

Pivot pin 114 is affixed and extends from C-shaped section 115 of camera support arm 55 which, in turn, is secured to bar 116 by means of screws 117 or the like. Bar 116 is rotatably mounted to frame section 118 by rod 119 which can be tightened by knurled knob 120 to lock frame section 118 in any desired position with relation to C-shaped section 115. Secured on the outer end of frame section 118 by means of screws 120 or the like is vertical adjustment means 121, which is comprised of cylinder 122 which, in turn, is threaded at its upper end 123.

Adjustment rod 124 passes through an opening in knurled cap 125, which is threaded on top 123 of cylinder 122, and is slidably received within cylinder 122. An elastic gasket 126 surrounds rod 124 and is positioned between cap 125 and cylinder 122. Ring clamp 58 is pivotably mounted on the top of adjustment rod 124 by means of pin 127 which can be tightened by lever 128 to lock ring clamp 58 at a desired angle. Ring clamp 58 is split with a threaded pin 129 therethrough which can be rotated by knurled knob 130 to thereby tighten or loosen ring clamp 58. The height of ring clamp 58 can be adjusted by loosening cap 125, extending or telescoping rod 124 within cylinder 122 to achieve the desired height, and then tightening cap 125 to compress elastic gasket into contact with rod 124 to thereby lock rod 124 at the desired height. Preferably, a spring 122a is positioned within cylinder 122 to lightly resist the telescoping of rod 124 to aid in the adjustment operation.

Referring now to FIG. 5, camera sleeve 56 is threaded at one end 131 which is adapted to be mated with a commercially-available T-adaptor 132 which, in turn, is adapted to be affixed into the lens receiving opening of a commercially-available camera back 57, e.g. 35 millimeter camera. Sleeve 56 has a thin wall which is slotted with H-shaped slots 133 to provide relative flexibility to sleeve 56. A circumferential groove 134 is provided on sleeve 56 which is adapted to receive spring-bias ball detent 135 (FIG. 10) in ring clamp 58 to retain sleeve in position within ring clamp 58. Light exclusion gasket 136, e.g. Teflon tape, is affixed to the inside of sleeve 56 for a reason discussed below.

To further describe the assembly and operation of the present invention, reference is again made to FIG. 1. In the first embodiment, original light source 30 and condenser lens 36 (FIG. 2) are removed from column 28a of a commercially-available slit lamp 10 and are replaced with illumination means 30a. Electrical leads 75 and 84 from a power source (not shown) are connected to lamp 69 and strobe 80, respectively. A preferred power source is of the type used for commercial photography, e.g. Model 202 Powerpack, Norman Enterprises, Los Angeles, Calif., modified slightly to supply the proper voltage, e.g. 0–12 volts, for lamp 69. As understood by those skilled in the art, a synchronization cord (not shown) is attached from the power source to camera 57 so that strobe 80 is activated when the shutter of camera 57 is tripped. Alternately, illumination means 30b or 30c can be assembled onto slit lamp 10 as previously described in place of illumiantion means 30a. The same type of power source will also be used with these embodiments.

Original ocular housing 90 is rmeoved from ocular 26a. and is replaced with ocular adaptor housing 91 as described above. Clamp 54 is attached to microscope support arm 25 and is designed to be left in position on slit lamp 10 once it is assembled thereon. Commercially-available T-adpator 132 (FIG. 5) is affixed to the lens opening of camera back 57 and sleeve 56 is screwed into T-adaptor 132. Sleeve 56 is then inserted into ring clamp 58 on camera support arm 55 until ball detent 135 engages groove 134 on sleeve 56. Pivot pin 114 is inserted in passage 113 of clamp 54 to pivotably mount camera support arm 55 on slit lamp 10.

By means of pivot pin 114, pivot rod 119, vertical adjustment means 121, and pivot pin 127, sleeve 56 within ring clamp 58 is brought into alignment with and is moved onto ocular 26a. Gasket 136 engages the smooth surface of ocular adaptor 59 to form a light-tight seal. Screw 129 is tightened to secure sleeve 56 in positon on ocular 26a and to further effect the sealing relationship between housing 59 and sleeve 56. Since eyepiece adjustment ring 91 is rotatable with respect to ocular adaptor housing 59, the examiner can properly focus ocular 26a by looking through the eyepiece of camera back 57. The shutter on camera back 57 which also simultaneously operates strobe 80 is actuated and a picture is taken through ocular 26a. By photographing directly through ocular 26a which can easily be focused even with camera back 57 in place, the original full range of magnification of slit lamp 10 is available for photography; this not being the case with known, commercially-available special slit lamp photography units. Further, when a slit image is to be photographed, the exit optical plate L (FIG. 1) is preferably removed and replaced with a rotatable plate (not shown) having a plurality of different lenses which compensate for the change in focal distance of the slit image to the object being photographed caused by the optics of the camera back 57 and the magnification power of the ocular through which the photograph is taken.

Clamp 54 has a lock means 140 (FIG. 10) thereon which comprises a spring-biased detent 141 extending from the lower end thereof which is adapted to engage passage 142 in C-shaped section 115 of camera support arm 55 to lock arm out of the way of the examiner when not in use. Detent 141 is released by lifting up on lever 143 which extends through a slot on lock means 140. Of course, if desired, entire camera support arm 55 can easily be removed from slit lamp 10 by merely lifting up on arm 55 to remove pivot pin 114 from passage 113 in clamp 54.

What is claimed is:

1. An assembly for converting a commercially-available slit lamp optical examination apparatus of the type having a microscope and an illumination column into an optical examination apparatus capable of taking photographs of the eye through at least one ocular of said microscope, said assembly comprising:
   a sleeve adapted to be connected into the lens opening of a camera;
   a clamp adapted to be secured onto the support for the microscope of said slit lamp apparatus;
   a camera support arm adapted to be pivotably connected to said clamp, said arm having a means thereon adapted to receive the outer surface of said sleeve to thereby attach said camera to said camera support arm;
   an ocular adaptor housing adapted to replace the original ocular housing of said ocular of said slit lamp apparatus, said ocular adaptor housing having a smooth outer surface adapted to receive the inner surface of said sleeve to thereby exclude external light from said sleeve; and
   an illumination means adapted to replace the original light source on said illumination column of said slit lamp apparatus, said illumination source comprising:
     a housing adapted to be connected onto said illumination column of said slit lamp apparatus;
     a steady light means in said housing for supplying the illumination necessary for a routine examination; and
     a strobe light means in said housing for supplying the illumination necessary for taking photographs through said ocular.

2. The assembly of claim 1 wherein said housing of illumination means comprises:
   an upper section having said steady light means mounted therein;
   a lower section having said strobe means mounted therein; and
   means for connecting said upper and lower sections together.

3. The assembly of claim 2 wherein said strobe means comprises:
   a ring-shaped strobe.

4. The assembly of claim 3 wherein said strobe means comprises:
   a cylindrical-shaped strobe.

5. The assembly of claim 1 wherein said housing comprises:
   a main support adapted to be positioned on said illumination column;
   means for suspending said strobe light means from said main support; and
   means for suspending said steady light means from said main support.

6. The assembly of claim 5, wherein said strobe light means comprises:
   a ring-shaped strobe, said strobe being suspended from said main support so that the diameter of said ring-shaped strobe will lie substantially along the longitudinal axis of said illumination column when said illumination means is in an operable position; and wherein said steady light means comprises:
   a bulb, said bulb being suspended from said main support so that it is positioned within the center of said ring-shaped strobe when in an operable position.

7. The assembly of claim 6 wherein said means for suspending said steady light means from said main support is adjustable to different positions on said main support.

8. The assembly of claim 1 wherein said camera support arm further comprises:
   a first section;
   means on said first section for pivotably connecting said camera support arm to said clamp;
   a second section pivotably connected to said first second section;
   releasable means for locking said first and second sections in a fixed position in relation to each other; and
   means on said second section for vertically adjusting said sleeve receiving means with respect to said second section.

9. The assembly of claim 8 wherein said vertical adjustment means comprises:
   a hollow cylinder attached to the outer end of said second section; said cylinder externally threaded on its upper end;
   a cap threaded onto said threaded end of said cylinder, said cap having a central opening therethrough;
   a rod carrying said sleeve receiving means on the upper end thereof, said rod passing through said opening in said cap and into said cyliner; and
   a compressible gasket surrounding said rod between said cap and said threaded end of said cylinder.

10. The assembly of claim 9 wherein said sleeve receiving means comprises:
    a ring clamp; and
    means for tightening or loosening said ring clamp.

11. In combination with a slit lamp optical examination apparatus of the type that has a microscope having at least one ocular carried by a microscope support and an illumination column, the improvements comprising:
    a clamp affixed to said microscope support;
    a camera support arm pivotably mounted on said clamp;
    means carried by said camera support arm for attaching a camera to said at least one ocular whereby said camera can take a photograph through said ocular; and
    an illumination means mounted on said illumination column, said illumination source comprising:
    a housing;
    a steady light means in said housing for supplying illumination for routine examinations; and
    a strobe light source in said housing for supplying illumination for photographing through said at least one ocular.

12. The apparatus of claim 11 wherein said housing comprising:
    an upper section having said steady light means mounted therein.

13. The apparatus of claim 12 wherein said strobe means comprises:
    a ring-shaped strobe.

14. The assembly of claim 12 wherein said strobe means comprises:
    a cylindrical-shaped strobe.

15. The assembly of claim 11 wherein said housing comprises:
    a main support adapted to be positioned on said illumination column;
    means for suspending said strobe light means from said main support; and
    means for suspending said steady light means from said main support.

16. The assembly of claim 15 wherein said strobe light means comprises:
    a ring-shaped strobe, said strobe being suspended from said main support so that the diameter of said ring-shaped strobe will lie substantially along the longitudinal axis of said illumination column when said illumination means is in an operable position; and wherein said steady light means comprises:
    a bulb, said bulb being suspended from said main support so that it is positioned within the center of said ring-shaped strobe when in an operable position.

17. The assembly of claim 16 wherein said means for suspending said steady light means from said main support is adjustable to different positions on said main support.

18. The apparatus of claim 11 wherein said camera support arm comprises:
    a first section;
    means on said first section for pivotably connecting said camera support arm to said clamp;
    a second section pivotably connected to said first section;
    releasable means for locking said first and second sections in a fixed position in relation to each other; and
    means on said section for vertically adjusting said camera attaching means in relation to said second section.

19. The apparatus of claim 18 wherein said vertical adjusting means comprises:
    a hollow cylinder attached to the outer end of said second section, said cylinder externally threaded on its upper end;
    a cap threaded onto said threaded end of said cylinder, said cap having a central opening therethrough;
    a rod carrying said camera attaching means on the upper end thereof, said rod passing through said opening in said cap and into said cylinder; and
    a compressible gasket surrounding said rod between said cap and said threaded end of said cylinder.

20. The apparatus of claim 19 wherein said camera attaching means comprises:
    a ring clamp mounted on the end of said rod; and
    a sleeve removably received within said ring clamp, said sleeve being adapted to be connected to one end to a lens receiving opening of a camera and having an inner surface adapted to receive said at least one ocular when in an operable position.

21. Apparatus for mounting a camera onto a slit lamp optic examination unit of the type having a microscope with at least one ocular mounted on a support, said apparatus comprising:
- a clamp adapted to be secured onto said microscope support;
- a first section;
- means on said first section for pivotably connecting said camera support arm to said clamp,
- a second section pivotably connected to said first section;
- releasable means for locking said first and second sections in a fixed position in relation to each other;
- camera attaching means carried by said second section; and
- means on said section for vertically adjusting said camera attaching means in relation to said second section.

22. The apparatus of claim 21 wherein said vertical adjusting means comprises:
- a hollow cylinder attached to the outer end of said second section, said cylinder externally threaded on its upper end;
- a cap threaded onto said threaded end of said cylinder, said cap having a central opening therethrough;
- a rod carrying said camera attaching means on the upper end thereof, said rod passing through said opening in said cap and into said cylinder; and
- a compressible gasket surrounding said rod between said cap and said threaded end of said cylinder.

23. The apparatus of claim 22 wherein said camera attaching means comprises:
- a ring clamp pivotably mounted on the end of said rod; and
- a sleeve removably received within said ring clamp, said sleeve being adapted to be connected to one end to a lens receiving opening of a camera and having an inner surface adapted to receive said at least one ocular when in an operable position.

* * * * *